(12) United States Patent
Fabian et al.

(10) Patent No.: US 10,881,407 B2
(45) Date of Patent: Jan. 5, 2021

(54) POSITIONING TOOL FOR ANASTOMOSIS

(71) Applicant: EasyNotes Ltd., Kfar Truman (IL)

(72) Inventors: Izhak Fabian, Kfar Truman (IL); Nir Altman, Kfar Etzion (IL); Steven Haas, Kochav Yair (IL); Yoav Hirsch, Modiin (IL); Ran Mendelewicz, Herzlia (IL)

(73) Assignee: EasyNotes Ltd., Kfar Truman (IL)

(*) Notice: Subject to any disclaimer, the term of this patent is extended or adjusted under 35 U.S.C. 154(b) by 0 days.

(21) Appl. No.: 15/181,501

(22) Filed: Jun. 14, 2016

(65) Prior Publication Data

US 2016/0287257 A1    Oct. 6, 2016

Related U.S. Application Data

(63) Continuation of application No. 13/862,431, filed on Apr. 14, 2013, now abandoned.

(51) Int. Cl.
*A61B 17/11* (2006.01)
*A61B 17/00* (2006.01)

(52) U.S. Cl.
CPC ... *A61B 17/1114* (2013.01); *A61B 2017/0034* (2013.01); *A61B 2017/00876* (2013.01); *A61B 2017/1117* (2013.01); *A61B 2017/1139* (2013.01)

(58) Field of Classification Search
CPC ........ A61B 17/1114; A61B 2017/0034; A61B 2017/00876; A61B 2017/1117; A61B 2017/1139; A61B 2017/111
See application file for complete search history.

(56) References Cited

U.S. PATENT DOCUMENTS

| | | | |
|---|---|---|---|
| 2005/0182429 A1* | 8/2005 | Yamanouchi | A61B 17/11 606/153 |
| 2006/0036267 A1* | 2/2006 | Saadat | A61B 17/11 606/153 |
| 2008/0208224 A1* | 8/2008 | Surti | A61B 17/1114 606/153 |
| 2010/0036399 A1* | 2/2010 | Viola | A61B 17/11 606/153 |
| 2010/0256659 A1* | 10/2010 | Aguirre | A61B 17/1114 606/153 |
| 2011/0144560 A1* | 6/2011 | Gagner | A61B 17/1114 604/8 |

\* cited by examiner

*Primary Examiner* — Tuan V Nguyen
(74) *Attorney, Agent, or Firm* — Dekel Patent Ltd.; David Klein

(57) ABSTRACT

An assembly including a positioning tool that includes a probe affixed to a portion of a grasping tool, wherein a distal tip of the probe protrudes distally from the grasping tool a distance corresponding to a position for placing a magnet with the grasping tool.

3 Claims, 1 Drawing Sheet

POSITIONING TOOL FOR ANASTOMOSIS

CROSS REFERENCE TO OTHER APPLICATIONS

This application is a continuation of U.S. patent application Ser. No. 13/862,431, filed Apr. 13, 2013, now abandoned.

FIELD OF THE INVENTION

The present invention generally relates to devices and methods for creating an anastomosis in the gastrointestinal (GI) tract, and particularly to a positioning aid for positioning a stomach anastomosis magnet relative to the pyloric valve (pylorus).

BACKGROUND OF THE INVENTION

Magnetic anastomosis devices are used to create a channel between two viscera for the purpose of redirecting bodily fluids. For example, intestinal contents or bile may be redirected in patients who have developed an obstruction of the bowel or bile duct due to such conditions as tumor, ulcer, inflammatory strictures or trauma. Some magnetic anastomosis devices include first and second magnet assemblies comprising magnetic cores that are surrounded by thin metal rims. Due to the magnetic attraction between the two magnetic cores, the walls of two adjacent viscera (e.g., the gall bladder, common bile duct, stomach, duodenum, or jejunum) may be sandwiched and compressed between the magnet assemblies, resulting in ischemic necrosis of the walls to produce an anastomosis between the two viscera.

SUMMARY OF THE INVENTION

The present invention seeks to provide a positioning aid for positioning a stomach anastomosis magnet relative to the pylorus, as is described more in detail hereinbelow.

There is thus provided in accordance with an embodiment of the present invention an assembly including a positioning tool that includes a probe affixed to a portion of a grasping tool, wherein a distal tip of the probe protrudes distally from the grasping tool a distance corresponding to a position for placing a magnet with the grasping tool. The assembly may further include a stomach anastomosis magnet that includes a holding portion for grasping with the grasping tool.

There is provided in accordance with an embodiment of the present invention a method including delivering a first magnet to a place in a stomach by grasping the first magnet with a grasping tool, wherein a positioning tool that includes a probe is affixed to a portion of the grasping tool, delivering a second magnet, either before or after delivery of the first magnet, to a place in an intestine past a pylorus, wherein a distal tip of the probe protrudes distally from the grasping tool a distance corresponding to a proper position for placing the first magnet in the stomach, and aligning the first and second magnets and releasing them so that magnetic forces attract the magnets together, compressing together walls of the intestine and the stomach for eventually forming an anastomosis.

BRIEF DESCRIPTION OF THE DRAWINGS

The present invention will be understood and appreciated more fully from the following detailed description taken in conjunction with the drawings in which.

DETAILED DESCRIPTION OF EMBODIMENTS

Figure 1:
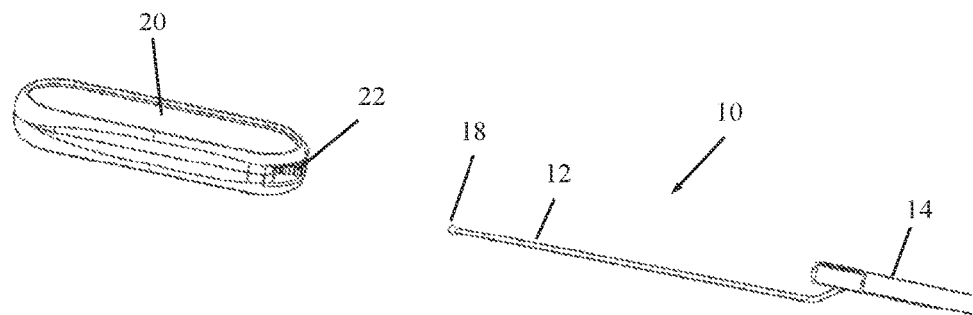
FIG. 1 is a simplified pictorial illustration of a positioning tool for use with a stomach anastomosis magnet, constructed and operative in accordance with an embodiment of the present invention.
Figure 2:
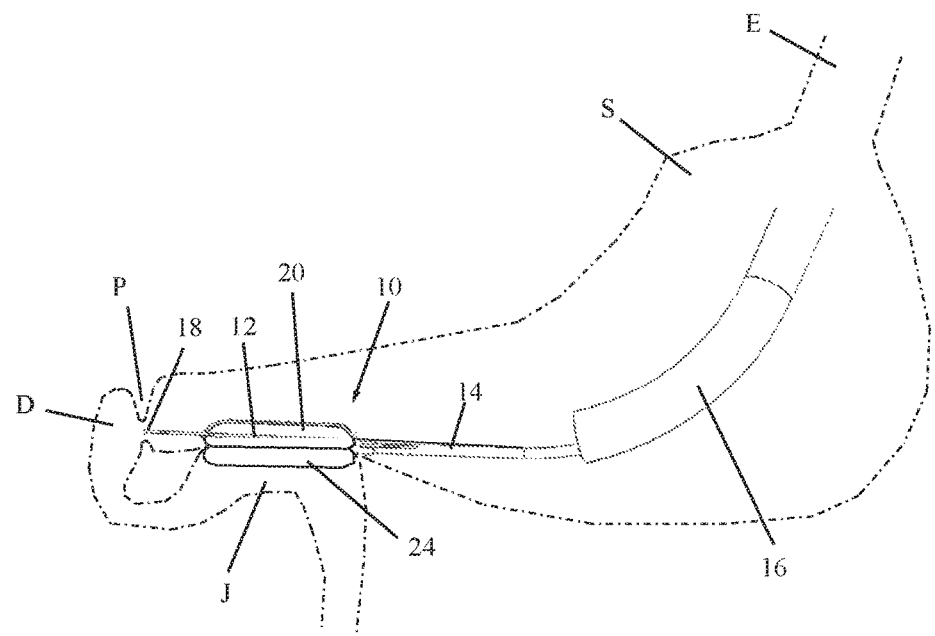
FIG. 2 is a simplified illustration of the positioning tool attached to the stomach anastomosis magnet and properly distanced from the pylorus, in accordance with an embodiment of the present invention.

Reference is now made to FIGS. 1 and 2, which illustrate a positioning tool 10 for use with a stomach anastomosis magnet 20, constructed and operative in accordance with an embodiment of the present invention.

The positioning tool 10 includes a probe 12 affixed to a portion of a grasping tool 14, such as but not limited to, a distal end of a biopsy forceps or other endoscopic tool which may be delivered through an endoscope 16 (shown in FIG. 2). The stomach anastomosis magnet 20 has a holding portion 22 for grasping with grasping tool 14.

Magnet 20 is shown having a general disc shape, but other shapes, such as but not limited to, cylindrical, polygonal, ovoid, cube and others, can also be used. Magnet 20 may include a protective coating (such as, but not limited to, polytetrafluoroethylene) for protection of the magnetic core from corrosive digestive acids or other bodily fluids.

FIG. 2 illustrates magnets placed for forming an anastomosis between the stomach and a portion of the small intestine (such as the duodenum, jejunum or ileum). In addition to magnet 20, another anastomosis magnet 24 has been delivered through the esophagus E, stomach S, pylorus P, duodenum D and jejunum J. Magnet 24 may be delivered by an endoscope, guidewire, catheter or other device, and is placed adjacent to the intestinal wall (e.g., of the jejunum) as shown in FIG. 2.

Magnet 20 is delivered to its place in the stomach by grasping with grasping tool 14 that passes through endoscope 16, or it can be delivered by guidewire, catheter or other device, in a similar manner to introducing magnet 24. Magnet 20 is positioned adjacent the wall of the stomach that borders the jejunum near the location of magnet 24. As seen in FIG. 2, the distance that probe 12 protrudes distally from grasping tool 14 is selected such that a distal tip 18 of probe 12 will touch the pylorus when stomach anastomosis magnet 20 is properly positioned opposite magnet 24. The position of magnet 24 may be modified by its delivery system to align with magnet 20. The magnets 20 and 24 may then be released so that the magnetic forces attract the magnets together, compressing together the walls of the jejunum and the stomach. Once necrosis of the walls of the stomach and the jejunum is complete, an anastomosis is formed. The magnets 20 and 24 can then pass through the body naturally or can be removed by means such as laparoscopic removal, endoscopic removal, or other procedure.

It will be appreciated by persons skilled in the art that the present invention is not limited by what has been particularly shown and described hereinabove. Rather the scope of the present invention includes both combinations and sub-combinations of the features described hereinabove as well as modifications and variations thereof which would occur to a person of skill in the art upon reading the foregoing description and which are not in the prior art.

What is claimed is:

1. A method comprising:
   delivering a first magnet to a place in a stomach by grasping said first magnet with a grasping tool, wherein a positioning tool that comprises a probe is affixed to a portion of said grasping tool;

delivering a second magnet, either before or after delivery of said first magnet, to a place in an intestine past a pylorus;

using said grasping tool to move a terminal distal end of said probe to touch the pylorus so that a position of said first magnet is at a fixed distance with respect to the pylorus;

adjusting a position of said second magnet to align said second magnet with said first magnet, wherein a distance between the terminal distal end of said probe and a terminal end of said grasping tool is nonadjustable; and releasing said first and second magnets so that magnetic forces attract said magnets together, compressing together walls of the intestine and the stomach for eventually forming an anastomosis.

2. The method according to claim 1, wherein adjusting a position of said second magnet to align said second magnet with said first magnet is done with a delivery system of said second magnet.

3. The method according to claim 1, wherein said probe has a width and a length at least five times longer than the width.

* * * * *